United States Patent [19]

Huang et al.

[11] Patent Number: 5,631,381
[45] Date of Patent: May 20, 1997

[54] PROCESS FOR THE PREPARATION OF PESTICIDAL 1-(HALOARYL) HETEROCYCLIC COMPOUNDS

[75] Inventors: Jamin Huang, Chapel Hill; Scot K. Huber, Raleigh, both of N.C.; Philip H. G. Smith; John H. Wilkinson, both of Ongar, United Kingdom

[73] Assignee: Rhone-Poulenc Inc., Research Triangle Park, N.C.

[21] Appl. No.: 671,691

[22] Filed: Jun. 28, 1996

Related U.S. Application Data

[63] Continuation-in-part of Ser. No. 426,656, Apr. 21, 1995, abandoned.

[51] Int. Cl.$^6$ .................................................. C07D 231/14
[52] U.S. Cl. .................... 548/367.4; 548/132; 548/221; 548/255; 548/257; 548/259; 548/260; 548/263.2; 548/264.8; 548/265.8; 548/316.4; 548/316.7; 548/327.5; 548/331.5; 548/361.1; 548/361.5; 548/362.1; 548/362.5; 548/366.4; 548/367.1; 548/371.4; 548/371.7; 548/483; 548/484; 548/485; 548/486; 548/490; 548/491; 548/541; 548/543; 548/544; 548/545; 548/557; 546/268.4; 546/269.1; 546/269.4; 546/271.7; 546/274.1; 546/275.4; 546/275.7; 546/276.1; 546/276.4; 546/277.1; 546/278.4; 546/279.1; 546/286; 546/288; 546/289; 546/290; 546/297; 544/336; 544/405; 544/408
[58] Field of Search .......................... 548/367.4, 132, 548/221, 255, 257, 259, 260, 263.2, 264.8, 265.8, 316.4, 316.7, 327.5, 331.5, 483, 484, 485, 486, 490, 491, 366.4, 367.1, 371.4, 371.7, 541, 543, 544, 545, 557, 361.1, 361.5, 362.1, 362.5; 546/268.4, 269.1, 269.4, 271.7, 274.1, 275.4, 275.7, 276.1, 276.4, 277.1, 278.4, 279.1, 286, 288, 289, 290, 297; 544/336, 405, 408

[56] References Cited

FOREIGN PATENT DOCUMENTS

| 0006999 | 1/1980 | European Pat. Off. . |
| 0396250 | 11/1990 | European Pat. Off. . |
| 0398499 | 11/1990 | European Pat. Off. . |
| 0534317 | 3/1993 | European Pat. Off. . |
| 2250986 | 6/1992 | United Kingdom . |
| 92/06964 | 4/1992 | WIPO . |

OTHER PUBLICATIONS

Beck, *Tetrahedron*, vol. 34, 2057–2068 (1978).
Williams, *J. Chem. Soc. Perkin Trans. II*, 1982, 801–804.
Ellison et al, *J. Chem. Soc. Perkin Trans. II*, 1981, 699–702.
March, *Advanced Organic Chemistry*, 2nd edition, Wiley, Interscience, New York, 1985, 77–79 and 468–470.
Sheppard, *J. Am. Chem. Soc.*, 1962, 84, 3064–3072.
Beaumont et al, *J. Fluorine Chem.*, 63, 25–30 (1993).
WPI Acc No 91-181440/25, abstract of JP 03109360, published May 9, 1991.
WPI Acc No 91-153798/21, abstract of JP 03090048, published Apr. 16, 1991.
WPI Acc No 91-099147/14, abstract of JP 03044335, published Feb. 26, 1991.
Maggini et al, *J. Org. Chem.* 56, 6406–6411 (1991).
Clark et al, *Chem. Ind.*, Jun. 17, 1991, 436.
Effenberger et al, *Chem. Ber.* 124, 157–162 (1991).
Suzuki et al, *Bull. Chem. Soc. Jpn.* 63, 2010–2017 (1990).
Yazawa et al, *Chem. Lett.* (12), 2213–2216 (1989).
Van der Puy, *J. Org. Chem.* 53, 4398–4401 (1988).
Egawa et al, *J. Heterocycl. Chem.* 24(1), 181–185 (1987).
Tanabe, *Nippon Kagaku Kaishi* (11), 2199–2201 (1985).
Milner, *Synth. Commun.*, 15(6), 485–489 (1985).
Enas, *J. Fluorine Chem.*, 63, 233–241 (1993).
Beaumont et al, *J. Fluorine Chem.*, 52, 295–300 (1991).
Passudetti et al, *J. Fluorine Chem.*, 50, 251–255 (1990).
Dence et al, *Appl. Radiat. Isot.*, 44(6), 981–983 (1993).
Bay et al, *J. Org. Chem.* 53, 2858–2859 (1988).
Fischer et al, *Helv. Chim. Acta*, 68, 854–859 (1985).
Platonov et al, *Journal of Organic Chemistry of the USSR, a translation of Zhurnal Organischeskoi Khimii*, 21(2), 345–353 (Eng.) corresp. to 383–391 (Russian), 1985.
Fischer et al, *Helv. Chim. Acta*, 68, 846–853 (1985).
Gorvin, *J. Chem. Res., Synop.* (7), 226–227 (1992).
Clark et al, *J. Fluorine. Chem.*, 70, 201–205 (Feb. 1995).

*Primary Examiner*—Joseph McKane
*Attorney, Agent, or Firm*—Burns, Doane, Swecker & Mathis, L.L.P.

[57] ABSTRACT

Process for preparing complex pesticidal 1-(haloaryl) heterocyclic compounds by reacting 1-(nitroaryl) heterocycles with metallic halide salts.

35 Claims, No Drawings

PROCESS FOR THE PREPARATION OF PESTICIDAL 1-(HALOARYL) HETEROCYCLIC COMPOUNDS

CROSS-REFERENCE TO RELATED APPLICATION

This is a continuation-in-part of prior U.S. patent application Ser. No. 08/426,656, filed Apr. 21, 1995, now abandoned incorporated by reference herein in its entirety and relied upon.

BACKGROUND OF THE INVENTION

1. Field of the Invention

The invention relates to a new process for the preparation of 1-(haloaryl)heterocyclic compounds and to novel compounds used in this process.

2. Background Art

A number of 1-(haloaryl)heterocyclic compounds useful as pesticides, particularly useful as insecticides, acaricides, nematicides, growth regulators, and/or herbicides, and the preparation thereof are known.

The manufacture of complex molecules, like the heterocyclic derivatives, is rather difficult and there is a need for a simple manufacturing process using simple reactants.

Formation of haloaryl compounds by reaction of nitroaryl compounds with halide salts is known in the literature, as described by James R. Beck, *Tetrahedron* 34, pp. 2057–2068 (1978) and references cited therein. Formation of 1-(2-halophenyl)pyrimidinones from 1-(2-nitrophenyl) pyrimidinones by halide-nitrite exchange is described in European Patent Publication No. 0396250. Such reactions, however, usually require long reaction times and high temperatures that decrease yields and increase the number of unwanted by-products.

It is therefore an object of the present invention to provide a new and efficient process for the preparation of 1-(haloaryl)heterocyclic compounds.

It is a further object of the invention to provide a process giving products substantially free of contaminating by-products.

Yet another object of the present invention is to provide a process for preparing such compounds in high yields.

These and other objects of the present invention will become apparent from the description that follows and are achieved in whole or in part by the present invention.

SUMMARY OF THE INVENTION

The present invention provides a process for the preparation of a heterocyclic compound of the formula:

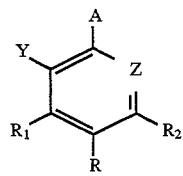

(I)

wherein:

R is haloalkyl, haloalkoxy, haloalkylsulfenyl, haloalkylsulfinyl, haloalkylsulfonyl, F, Cl, Br, I or $SF_5$;

$R_1$ and $R_2$ are each independently hydrogen, F, Cl, Br or I;

Y is F, Cl, Br or I;

Z is N, C—$NO_2$ or C—$R_3$ wherein $R_3$ is H, F, Cl, Br, I, CN, C(O)$NH_2$, C(S)$NH_2$, alkyl or haloalkyl;

and A represents an optionally substituted N-linked nitrogen-containing, five- or six-membered heterocyclic ring;

said process comprising reacting a nitro-containing compound of the formula:

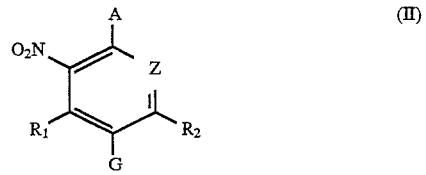

(II)

wherein $R_1$, $R_2$, Z and A are defined as above, and G is haloalkyl, haloalkoxy, haloalkylsulfenyl, haloalkylsulfinyl, haloalkylsulfonyl, F, Cl, Br, I, $SF_5$ or $NO_2$; with a metallic halide of the formula $MX_n$ wherein M is a metal cation, X is a halide anion and n is a positive integer equal to the valence of the metal cation, in the presence of a nitrite ion scavenging agent.

DETAILED DESCRIPTION OF THE INVENTION

Here and throughout this description, the following definitions are applicable, unless otherwise specified:

The word "halo" or "halogen" means F, Cl, Br or I. When the word "halo" is used in conjunction with a hydrocarbon, for example, "haloalkyl", one or more halo atoms are present on the hydrocarbon moiety.

The term "halide anion" means $F^-$, $Cl^-$, $Br^-$ or $I^-$.

The alkyl radicals and alkyl portions of other radicals (e.g. haloalkyl, haloalkoxy and so forth) generally have 1 to 7 carbon atoms. The word "lower" when used in conjunction with such radicals means the radicals have 1 to 4 carbon atoms.

The word "sulfenyl" means "thio"; for example, the terms "haloalkylsulfenyl" and "haloalkylthio" are synonymous.

The cycloalkyl and cycloalkenyl radicals and such portions of other radicals generally have 3 to 6 carbon atoms in the ring.

The alkenyl and alkynyl radicals and such portions of other radicals generally have 2 to 7 carbon atoms, preferably 2 to 4 carbon atoms.

In the process of the present invention, certain features in the starting materials and products are preferred, as noted below:

When R is haloalkyl, haloalkoxy, haloalkylsulfenyl, haloalkylsulfinyl or haloalkylsulfonyl, the alkyl portions thereof are preferably lower alkyl. R is preferably halogen or $SF_5$ or lower haloalkyl. Most preferably, R is $CF_3$ or $SF_5$.

$R_1$ and $R_2$ preferably are both H.

Y is preferably F, Cl or Br, most preferably Cl.

Z is preferably C—$NO_2$, C—Cl, C—H, C—Br, C—F or C—CN.

When G is haloalkyl, haloalkoxy, haloalkylsulfenyl, haloalkylsulfinyl or haloalkylsulfonyl, the alkyl portions thereof are preferably lower alkyl. G is preferably halogen, $SF_5$ or lower haloalkyl. Most preferably, G is $CF_3$ or $SF_5$.

The heterocyclic ring system represented by A can have the formula:

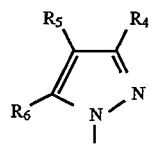 (a)

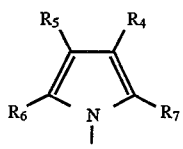 (b)

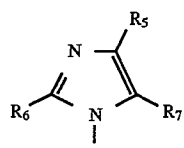 (c)

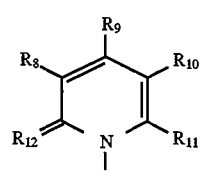 (d)

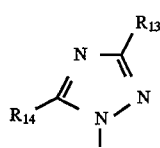 (f)

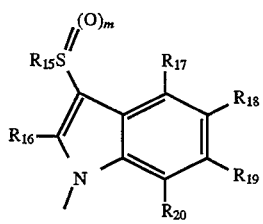 (g)

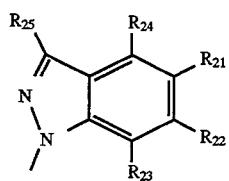 (h)

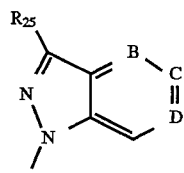 (i)

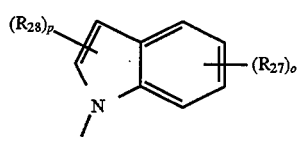 (j)

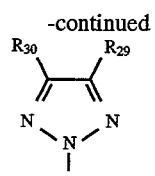 (k)

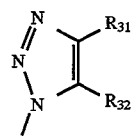 (l)

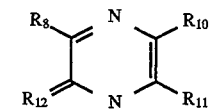 (m)

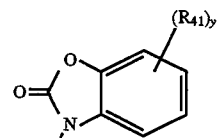 (n)

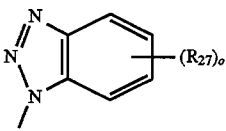 (p)

(q)

wherein:

$R_4$ is H, alkyl, haloalkyl, formyl, alkylcarbonyl, halogen, CN, $NO_2$, cycloalkyl, $C(O)NH_2$, alkoxy or $C(S)NH_2$;

$R_5$ is $R_{33}S(O)_q$, CN, SCN, $NO_2$, haloalkyl, haloalkylcarbonyl, haloalkoxy or halogen;

$R_6$ is H, alkyl, haloalkyl, alkylcarbonyl, formyl, haloalkylcarbonyl, halogen, $NR_{34}R_{35}$, alkylsulfenyl, alkylsulfinyl, alkylsulfonyl, alkoxy, haloalkoxy, N=CH—O-alkyl, or N=CH-(phenyl optionally substituted with OH, alkoxy, halogen, alkyl, haloalkyl, CN or $NO_2$);

$R_7$ is H, alkyl, haloalkyl, halogen, cyano, alkylsulfenyl, alkylsulfinyl, alkylsulfonyl, haloalkylsulfenyl, haloalkylsulfinyl or haloalkylsulfonyl;

$R_9$ is haloalkyl, CN, $NO_2$, halogen, H, alkylsulfenyl, alkylsulfinyl, alkylsulfonyl, haloalkylsulfenyl, haloalkylsulfinyl, haloalkylsulfonyl or haloalkoxy;

$R_8$, $R_{10}$ and $R_{11}$ are each independently H, alkyl, halo, CN, $NO_2$ or haloalkyl;

$R_{12}$ is O or S;

$R_{13}$ is alkyl, optionally substituted by halogen, alkoxy, alkylthio, alkylsulfonyl, alkoxycarbonyl, carbamoyl, cycloalkyl or alkenyl;

$R_{14}$ is H, halogen, haloalkyl, alkoxyalkyl, alkenyloxyalkyl, methyl, alkylsulfenyl, alkylsulfinyl, alkylsulfonyl or $NR_{34}R_{35}$;

$R_{15}$ is alkyl or haloalkyl;

$R_{16}$, $R_{17}$, $R_{18}$, $R_{19}$ and $R_{20}$ are each independently H, alkyl, alkenyl, alkynyl, halogen, CN, formyl, alkylcarbonyl, alkoxycarbonyl, haloalkoxycarbonyl, haloalkylcarbonyl, $NO_2$, SCN, haloalkyl, alkoxy, haloalkoxy, haloalkenyl, alkylsulfenyl, alkylsulfinyl, alkylsulfonyl, haloalkylsulfenyl, haloalkylsulfinyl or haloalkylsulfonyl;

$R_{21}$, $R_{22}$ and $R_{24}$ are each independently H, halogen, $NO_2$, OH, CN, alkyl, alkoxyiminoalkyl, alkoxyalkyl, haloalkyl or alkoxy;

one of B, C and D is N or N→O and the others of B, C and D are each C—$R_{36}$;

$R_{23}$ is H, halogen, alkyl or $NO_2$;

$R_{25}$ is H or halogen;

$R_{27}$ is H; halogen; $NO_2$; CN; alkyl; alkoxy; alkenyloxy; alkynyloxy; alkoxyalkyl; carbonylalkoxy; alkyloxyalkoxy; cyanoalkoxy; benzyloxy; alkoxycarbonylalkoxy; alkylcarbonylalkoxy; haloalkyl; hydroxyalkyl; formyl; azido; COOH or a salt thereof; COO-alkyl; $NH_2$, which is optionally substituted by alkyl, alkoxy, OH, formyl, alkylcarbonyl (optionally substituted by COOH or alkoxycarboxy), alkylsulfonyl, haloalkylsulfonyl, aminocarbonyl, dialkylaminocarbonyl, alkoxycarbonyl, alkoxyalkyl, hydroxycarbonylalkyl, alkoxycarbonylalkyl, amino or dialkylamino; carboxamido, which is optionally substituted by alkyl or haloalkylsulfonyl; sulfonamido in which the N is substituted by H and/or alkyl; or $QR_{38}$;

$R_{28}$ is H, alkyl, halogen, CN, haloalkyl or alkoxy, or COOH or a salt or ester thereof;

$R_{29}$ and $R_{30}$ are each independently hydrogen, alkyl, alkenyl, alkynyl (wherein alkyl, alkenyl and alkynyl are each optionally substituted with halogen), phenyl, pyridyl, cyano, halogen, nitro, CHO, or $NR_{39}R_{40}$;

$R_{31}$ and $R_{32}$ are each independently H, halogen, CN, $NO_2$, $CONH_2$, alkylsulfinyl, alkylsulfonyl, alkylsulfenyl or $NR_{34}R_{35}$;

$R_{33}$ is $C_1$–$C_6$ alkyl, cycloalkyl, cycloalkylalkyl or haloalkyl;

$R_{34}$ and $R_{35}$ are each independently H, alkyl, alkylcarbonyl, formyl or alkoxycarbonyl, or $R_{34}$ and $R_{35}$ together with the nitrogen atom to which they are attached form a 5-membered pyrrole or pyrazole moiety;

$R_{36}$ is H, halogen, $NO_2$, CN, alkyl, alkoxyalkyl, acetoxymethyl, hydroxymethyl, haloalkyl, formyl, alkylcarbonyl, carboxy or a salt thereof, COO-alkyl, $N_3$, $NH_2$ (optionally substituted by alkyl, alkoxy, OH, formyl, alkylcarbonyl, alkoxycarbonylalkyloxy, alkoxycarbonylalkylthio, alkoxycarbonylalkylidenecarbonyl, hydroxycarbonylalkoxy, hydroxycarbonylthio, cyanoalkoxy, hydroxycarbonylalkylidenecarbonyl, alkylsulfonyl, haloalkylsulfonyl, aminocarbonyl, dialkylaminocarbonyl, alkoxycarbonyl, alkoxyalkyl, hydroxycarbonylalkyl, alkoxycarbonylalkyl or amino), carboxyamido (optionally substituted by alkyl, alkylsulfonyl or haloalkylsulfonyl), sulfonamido (in which the N is substituted by H and/or alkyl) or $QR_{37}$;

$R_{37}$ is H, alkyl, haloalkyl, cyanoalkyl, alkoxycarbonylalkyl, hydroxycarbonylalkyl or aminocarbonylalkyl (in which the N is substituted by H and/or alkyl);

Q is O or $S(O)_m$;

$R_{38}$ is H, haloalkyl, cyanoalkyl, alkoxycarbonylalkyl, hydroxycarbonylalkyl or aminocarbonylalkyl (in which the N is substituted by H and/or alkyl);

$R_{39}$ and $R_{40}$ are independently each hydrogen, optionally substituted alkyl, acyl or aryl, or together with the nitrogen to which they are attached, form a 5- to 7-membered ring which optionally has other hetero ring atoms;

$R_{41}$ is hydrogen, alkyl, alkoxy, alkenyloxy, alkynyloxy, carboxyalkoxy, alkoxycarbonylalkoxy, alkoxyalkoxy, cyanoalkoxy, haloalkylsulfonylamino, alkylsulfonylamino, alkoxycarbonyl, haloalkyl, halogen, nitro, carboxy, carboxyalkyl, hydroxy, benzyloxy or cyano;

$R_{42}$ is $C_7$ bicycloalkyl, methyl- or chloro-substituted $C_3$–$C_6$ cycloalkyl, $C_2$–$C_5$ alkenyl, methyl-substituted $C_6$ cycloalkenyl, 2-methyl-1,3-dithiolan-2-yl or $C_1$–$C_5$ alkyl, wherein alkyl is optionally substituted with halogen, $C_1$–$C_3$ alkoxy, $C_1$–$C_3$ alkylthio, $C_1$–$C_3$ alkylsulfinyl, $C_1$–$C_3$ alkylsulfonyl or $C_1$–$C_3$ alkoxycarbonyl;

m is 0, 1 or 2;

o is 0, 1, 2, 3 or 4;

p is 0, 1 or 2;

q is 0, 1 or 2; and y is 0, 1, 2 or 3.

It will be understood that structures (a)–(q) can give rise to stereoisomers and optical isomers. All such forms are embraced by the present invention.

In formulae (a) to (q) above the unattached single bond represents the point of attachment of the heterocyclic ring system in formulas (I) and (II) and Schemes (I) and (II).

A is preferably an optionally substituted pyrrolyl, pyrazolyl or imidazolyl ring linked through a nitrogen atom thereof, more preferably a pyrazolyl ring.

Among structures (a) through (q) depicted above, A preferably has structure (a), (b) or (c).

Metal halide salts $MX_n$ suitable for use in the present invention include metal halide salts, for example, in which M is an alkali metal cation or alkaline earth metal cation and n is 1 or 2. Representative metal halide salts for use herein include LiCl, NaCl, KCl, CsCl, $MgCl_2$, LiBr, NaBr, KBr, CsBr, $MgBr_2$, LiF, NaF, KF, CsF, LiI, NaI, KI, CsI, $MgI_2$ and $ZnI_2$. Preferred $MX_n$ derivatives are alkali metal halides, especially LiCl, NaCl, KCl, CsCl, LiBr, NaBr, KBr, NaF or KF. The most preferred $MX_n$ for use herein is LiCl.

One of the preferred embodiments of the present invention comprises reacting a compound of formula (II) above with at least 1 molar equivalent, preferably from about 1 to about 10 molar equivalents, of the metal halide salt $MX_n$. The presence of a solvent is advantageous. The reaction is generally run within a temperature range of from about 50° to about 250° C. and optionally in the presence of from about 1 to about 10 molar equivalents of a metal-chelating additive. Metal-chelating additives are compounds which form a complex with the metal halide salt $MX_n$, thus increasing the reactivity of the halide anion as described in March, *Advanced Organic Chemistry*, 2nd Edition, Wiley, Interscience; New York; 1985; pages 77–79. Metal chelating additives preferred for the present invention are, for example, 12-crown-4, 15-crown-5, 18-crown-6, and tris(3, 6-dioxaheptyl)amine (TDA-1).

Reagents able to destroy or remove a nitrite ion are known in the art (Williams, *J. Chem. Soc. Perkin Trans.* II, 1982, pages 801–804 and references cited therein; Ellison and Williams, Ibid., 1981, pages 699–702 and references cited therein). Preferred such adjuvants, designated in abbreviations as nitrite ion scavenging reagents, for use in the present invention are sulfamic acid, urea, aniline, hydroxylamine, hydrazine, hydrazoic acid, ascorbic acid, ammonium sulfamate or ammonia. Nitrite ion scavenging reagents can be present in an amount of from about 1 to about 3 molar equivalent per mole of starting reactant.

Reaction solvents suitable for use in the present invention include organic solvents which are inert under the reaction conditions, such as a chlorinated hydrocarbon, ether, polyether, hydrocarbon or polar aprotic solvent, or a mixture of two or more of the foregoing. Preferred reaction solvents are, for example, N-methylpyrrolidinone (NMP), dimethylformamide (DMF), dimethylsulfoxide (DMSO), hexamethylphosphoric triamide (HMPA) and sulfolane.

According to an embodiment of the present invention, a dinitro compound of formula (II) in which Z is —$NO_2$ is reacted with a metal halide salt $MX_n$ under the conditions described above to form a halogenated compound wherein either one or two nitro groups have been replaced by a halogen atom. When two nitro groups are thus caused to react, the second one is preferably caused to react at temperatures higher than 80° C. and/or with LiCl as the metal halide agent.

A further embodiment of the present invention comprises reacting a dinitro compound of formula (II) in which Z is —$NO_2$ with a metal halide salt $MX_n$ under the conditions described above to form a mono-halo, mono-nitro compound and then reacting the resultant mono-halo, mono-nitro compound again under the conditions described with a metal halide salt $M'X'_n$, (which is either the same as or different from $MX_n$), either by adding the metal halide salt $M'X'_n$ to the same pot, or by sequentially reacting the dinitro compound with $MX_n$, and then reacting the mono-nitro compound formed with $M'X'_n$ in separate pots, to form a compound of formula (I).

The halogenated compounds of formula (I) can be isolated by conventional techniques such as dilution of the reaction mixture with water and filtration or, alternatively, extraction with a suitable solvent. Suitable extraction solvents include water immiscible solvents such as methyl tert-butyl ether (MTBE), diethyl ether, ethyl acetate (EtOAc), toluene, methylene chloride and the like.

In general, compounds of formula (II) are known compounds, or can be prepared by well-known methods or by modifications of well-known methods. Compounds of formula (II) and methods for their preparation are described, for example, in WO 87/03781; WO 94/21606; EP 0398499; JP 05262741; U.S. Pat. No. 5,306,694; EP 0201852; DE 3529829; DE 3501323; DE 3538731; DE 3606476; DE 3609423; EP 0350311; DE 3617554; DE 3402308; U.S. Pat. Nos. 4,496,390; 4,459,150; 4,629,495; 5,223,525; JP 05025138; EP 0464980; EP 0445931; EP 0367410; EP 0272824; EP 0338686; U.S. Pat. No. 5,104,878; EP 0357201; EP 0481604; EP 0396250; EP 0285893; JP 02091062; JP 06092935; WO 93/8008; U.S. Pat. No. 5,300, 478; WO 93/15049; U.S. Pat. No. 5,064,844; EP 0408196; EP 0400842; U.S. Pat. No. 5,232,899; EP 0438209; WO 94/25446; and EP 0435616.

For example, compounds of formula (II) can be prepared by reacting a compound of the formula (IV), wherein A is defined hereinabove, with a nitroaryl compound of formula (III), in the presence of a base, preferably a mineral base such as sodium bicarbonate or an amine base such as triethylamine, where L is a leaving group which may be, for example, a halide ion, $F^-$, $Cl^-$, $Br^-$, or $I^-$, or an alkylsulfonate anion or a phenylsulfonate anion, or nitrite ion, according to the following Scheme I:

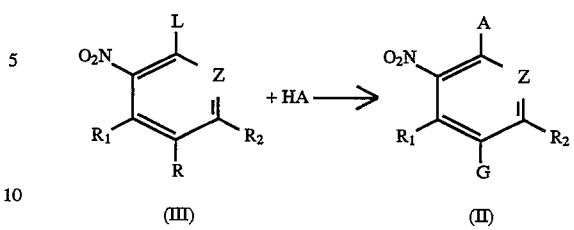

Scheme I

In a further example, compounds of formula (II) can also be prepared by cyclization to form the heterocyclic portion A as defined above onto an aniline of the formula (IV) below in one or more stages, as depicted in the following Scheme II:

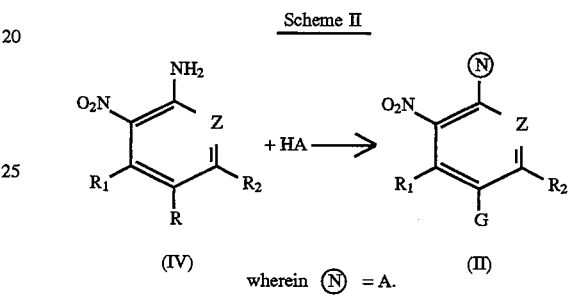

Scheme II

Compounds of formulas (II) and compounds of formula (II) in which A is selected from (a), (b), or (c) and in which R is $SF_5$ can furthermore be prepared by the methods described below. For example, a particularly useful preparation of compounds of formula (II) in which R is $SF_5$ is by nitration of the known compound, 4-chloro-1-(pentafluorosulfenyl)benzene or 4-fluoro-1-(pentafluorosulfenyl)benzene (William A. Sheppard, *J. Am. Chem. Soc.*, 1962, 84, pp. 3064–3072) under standard conditions (March, *Advanced Organic Chemistry*, pp. 468–470 and references cited therein); or by modification of standard conditions in a manner obvious to one skilled in the art, to form 4-chloro- or 4-fluoro-3,5-dinitro-1-(pentafluorosulfenyl)benzene, followed by reaction of the resultant 4-chloro- or 4-fluoro-3,5-dinitro-1-(pentafluorosulfenyl)benzene with a compound of the formula H-A (wherein A is a heterocyclic moiety as defined hereinabove) in the coupling manner described. Many 1-H-heterocyclic compounds are disclosed in the prior art cited above.

Compounds of formula (II) wherein A is (b) as defined above; G is haloalkyl, haloalkoxy, haloalkylsulfenyl, haloalkylsulfinyl, haloalkylsulfonyl, F, Cl, Br, I, $SF_5$ or $NO_2$; $R_1$ and $R_2$ are each independently hydrogen, F, Cl, Br or I; Z is N, C—$NO_2$ or C—$R_3$ wherein $R_3$ is H, F, Cl, Br, I, CN, $C(O)NH_2$, $C(S)NH_2$, alkyl or haloalkyl are novel and useful intermediates and thus form a further feature of the invention. Such compounds may be prepared by the schemes shown above.

In order to further illustrate the present invention and the advantages thereof, the following specific examples are given, it being understood that same are intended only as illustrative and in no way limitative.

DETAILED EXAMPLES OF COMPOUND SYNTHESIS

EXAMPLE 1

Preparation of 2-chloro-3-cyano-1-(2,6-dichloro-4-trifluoromethylphenyl)-4-(dichlorofluoromethylsulfenyl)-5-methylpyrrole (a) 1-(2,6-Dinitro-4-trifluoromethylphenyl)-2-chloro-3-cyano-4-dichlorofluoromethylsulfenyl-5-methylpyrrole (1 g) in 10 ml of N-methyl pyrrolidinone was treated with lithium chloride (0.5 g) and sulfamic acid (1.0 g) and heated to 135°–138° C. After 23 h, the mixture was cooled to room temperature, poured into 100 ml of water, and extracted with methyl tert-butyl ether. The combined extracts were washed with brine and dried over magnesium sulfate. After filtering and removal of solvents, purification by silica gel chromatography afforded the title compound (0.47 g, 50% yield) and 1-(2-chloro-6-nitro-4-trifluoromethylphenyl)-2-chloro-3-cyano-4-(dichlorofluoromethylsulfenyl)-5-methylpyrrole (0.16 g, 15% yield).

(b) Comparative example in the absence of a nitrite ion scavenging agent 1-(2,6-Dinitro-4-trifluoromethylphenyl)-2-chloro-3-cyano-4-dichlorofluoromethylsulfenyl-5-methytpyrrole (1 g) in 10 ml of N-methyl pyrrolidinone was treated with lithium chloride (0.5 g) and heated to 135°–138° C. After 23 h, the mixture was cooled to room temperature, poured into 100 ml of water, and extracted with 75 ml of methyl tert-butyl ether which formed an intractable emulsion. About 25 ml of ethereal supernatant were separated, and the emulsion was filtered through a pad of Celite with no improvement. The emulsion was extracted as well as possible with 3×75 ml of methyl tert-butyl ether. The combined extracts were washed with brine and dried over magnesium sulfate. After filtering and removal of solvents, purification by silica gel chromatography afforded the title compound (0.19 g, 20% yield) with traces of 2-chloro-3-cyano-1-(2-chloro-6-hydroxy-4-trifluoromethylphenyl)-4-(dichlorofluoromethyl)sulfenyl-5-methylpyrrole.

The experiments above, which were conducted under identical conditions other than the presence or absence of a nitrite ion scavenging agent illustrate that the use of a nitrite ion scavenging agent according to the invention provides improved yields (compare 50% versus 20%), a simple purification, and removes contaminating by-products.

(c) A solution of 1-(2,6-dinitro-4-trifluoromethylphenyl)-2-chloro-3-cyano-4-dichlorofluoromethylsulfenyl-5-methylpyrrole (1.5 g) and lithium chloride (1.8 g) in 20 ml of dimethylsulfoxide was heated at 90° C. for 12 hours, then at 150° C. for 24 hours. The resulting brown mass was partitioned between ethyl acetate and water, filtered and separated. The organic phase was dried over MgSO$_4$, filtered and evaporated. Purification by silica gel chromatography afforded the title compound (0.44 g, 30% yield), m.p. around 138° C.

The following is a further comparative example in the presence of a nitrite ion scavenging agent.

(d) A solution of 1-(2,6-dinitro-4-trifluoromethylphenyl)-2-chloro-3-cyano-4-dichlorofluoromethylsulfenyl-5-methylpyrrole (1.0 g), lithium chloride (0.25 g) and sulfamic acid (0.38 g) in 10 ml of N-methyl pyrrolidinone was heated at 135° C. for 3 days. After cooling to room temperature, the mixture was diluted with water and extracted with 2×75 ml of methyl tert-butyl ether. The combined extracts were dried over MgSO$_4$, filtered and concentrated under reduced pressure. Purification by silica gel chromatography provided the title compound (0.82 g, 85% yield), m.p. around 138° C.

This illustrates the high yields that can be obtained using a nitrite ion scavenging agent.

EXAMPLE 2

Preparation of 1-(2-chloro-6-nitro-4-trifluoromethylphenyl)-2-chloro-3-cyano-4-(dichlorofluoromethylsulfenyl)-5-methylpyrrole A solution of 1-(2,6-dinitro-4-trifluoromethylphenyl)-2-chloro-3-cyano-4-dichlorofluoromethylsulfenyl)-5-methylpyrrole (47.36 g), lithium chloride (7.9 g), and sulfamic acid (9.06 g) in 200 ml of N-methyl pyrrolidinone was heated to 120° C. After 3 hours, additional lithium chloride (8.26 g) was added. After 2 hours, the mixture was cooled to room temperature, poured into 1.5 L of water, and extracted with methyl tert-butyl ether. The extracts were dried over MgSO$_4$, filtered through a plug of alumina and evaporated to afford the title compound (38.3 g, 83% yield) m.p. around 118° C.

EXAMPLE 3

Preparation of 5-amino-3-cyano-4-(trifluoromethylsulfenyl)-1-(2,6-dichloro-4-trifluoromethylphenyl)pyrazole A solution of 5-amino-3-cyano-4-(trifluoromethylsulfenyl)-1-(2,6-dinitro-4-trifluoromethylphenyl)pyrazole (0.4 g), lithium chloride (0.2 g), and sulfamic acid (0.18 g) in 8 ml of N-methylpyrrolidinone was heated at 135° C. for 2 days, then at 175° C. for 6 hours. The cooled reaction mixture was poured into 100 ml of ether and washed with 4×25 ml of water. The aqueous washings were extracted with 2×25 ml of ether. The combined ethereal solutions were dried over MgSO$_4$, filtered and evaporated to a yellow oil. Purification by column chromatography provided the title compound (0.18 g, 48% yield), m.p. around 161° C.

The following non-limiting Examples 4 and 5 illustrate the preparation of intermediates useful in the processes of the invention.

EXAMPLE 4

Preparation of 1-(2,6-dinitro-4-trifluoromethylphenyl)-2-chloro-3-cyano-4-dichlorofluoromethylsulfenyl-5-methylpyrrole Step A: Preparation of 2-chloro-3-cyano-5-methylpyrrole Hydrogen chloride was bubbled through a solution of 2-cyano-4-oxopentanenitrile (2.1 g) in 20 ml of CH$_2$Cl$_2$ and 20 ml of dioxane for 15 min. The mixture was stirred for 1.5 h, then poured into water and extracted with methylene chloride. The organic extracts were dried over MgSO$_4$. Purification by silica gel chromatography provided the title compound (3.1 g), m.p. around 157° C.

Step B: Preparation of 2-chloro-3-cyano-4-thiocyanato-5-methylpyrrole

A solution of sodium thiocyanate (1.5 g) in 10 ml of methanol was cooled to −70° C. Bromine (0.4 ml) in methanol (9 ml) was added dropwise over 17 min. A solution of the product of Step A (1.0 g) in 12 ml of methanol was cooled in the cooling bath, then added in one portion. The reaction was allowed to warm to room temperature over 2 h, quenched with a small amount of water, then poured into 200 ml of water. The resulting precipitate was filtered, washed with water and hexane, and air-dried to afford 1.2 g of the title compound, m.p. around 171° C.

Step C: Preparation of 4-(2-chloro-3-cyano-5-methylpyrrole)disulfide

A solution of the product of Step B (2.4 g) in 30 ml of methanol was cooled in an ice bath and treated with sodium borohydride (1.06 g) in portions over 40 min. The mixture was then heated to reflux for 40 min., cooled to room temperature and diluted with water. The resulting solid was collected by filtration, washed with water and hexane, and air-dried to afford 1.01 g of the title compound, m.p.>230° C. (decomp.).

Step D: Preparation of 2-chloro-3-cyano-4-(dichlorofluoromethyl)sulfenyl-5-methylpyrrole)

A solution of the product of Step C (1.6 g) in 50 ml of N-methyl pyrrolidinone in a pressure bottle was heated with sodium bicarbonate (1.92 g). Fluorotrichloromethane (17 ml) was added, the mixture cooled to −50° C. and sulfur dioxide (8 ml) was added. After warming to room temperature and stirring overnight, the mixture was vented. Nitrogen gas was bubbled through the mixture for 2 h and the solvent was then removed under reduced pressure. The resulting brown oil was dissolved in ethyl acetate, washed with water, and dried over $MgSO_4$. Purification by silica gel chromatography afforded 1.07 g of the title compound, m.p. around 187° C.

The product of Step D (1 g), 3,5-dinitro-4-fluorobenzotrifluoride (2 g) and anhydrous potassium carbonate (0.56 g) in sulfolane were combined and heated at 75° C. for 12 hr, poured into water, and washed with diethyl ether. The combined ether extracts were washed with water, dried over $MgSO_4$, filtered and concentrated in vacuo. The residue was purified via silica gel chromatography to provide 1-(2,6-dinitro-4-trifluoromethylphenyl)-2-chloro-3-cyano-4-dichlorofluoromethylsulfenyl-5-methylpyrrole (1.3 g), m.p. around 153° C.

EXAMPLE 5

Preparation of 5-amino-3-cyano-1-(2,6-dinitro-4-trifluoromethylphenyl)-4-trifluoromethylsulfenylpyrazole Step A: Preparation of 1-(N-tert-butoxycarbonyl)-3-ethoxycarbonyl-5-aminopyrazole The sodium anion of ethyl(2-oxy-3-cyano)propionate (55.0 g, 338 mmoles) was dissolved in 50 ml of water. The solution was diluted with 300 ml of ethanol, 29 ml of concentrated aqueous hydrochloric acid (12N) were added, and the resulting solution was stirred at room temperature for 15 min. 44.0 g of tert-butyl carbazate were added and the mixture was stirred at room temperature for 1.5 hrs. Another 14.2 g of tert-butyl carbazate were added and the mixture was stirred at room temperature for another 3 hrs. A solution of 25 g of potassium carbonate in 20 ml of water was slowly added at 0° C. and the resulting solution was refluxed for 30 min. The mixture was then concentrated, diluted with ethyl acetate and washed several times with water and brine. The organic layer was dried over $MgSO_4$ and concentrated to dryness to give 73.5 g of the title compound as a solid. $^1H$ NMR 300 MHz (DMSO-$d_6$): 1.28 (t, 3H); 1.58 (s, 9H); 4.26 (q, 2H); 5.67 (s, 1H); 6.49 (s, 2H).

Step B: Preparation of 1-(N-tert-butoxycarbonyl)-3-ethoxycarbonyl-4-trifluoromethylsulfenyl-5-aminopyrazole The product of Step A (80.9 g, 317 mmoles) was dissolved in 500 ml of dichloromethane. 28.5 ml of $CF_3SCl$ (1.05 eq) were slowly added at −60° C., then the yellow solution was stirred for 3 hrs. and concentrated to dryness to give 88.8 g of the title compound. $^1H$ NMR 300 MHz (DMSO-$d_6$): 1.28 (t, 3H); 1.58 (s, 9H); 4.26 (q, 2H); 7.23 (s, 2H); $^{19}F$ NMR 828 MHz (DMSO-$d_6$): −44.15, singlet.

Step C: Preparation of 1-(N-tert-butoxycarbonyl)-3-formyl-4-trifluoromethylsulfenyl-5-aminopyrazole The product of Step B (88.8 g, 250 mmoles) was dissolved in 200 ml of dry $CH_2Cl_2$, then diluted with 800 ml of methyl tert-butyl ether and cooled to 70° C. 425 ml of diisobutylaluminum hydride (1.5M in toluene) were added dropwise over an hour. The solution was stirred at −50° C. for 1 hour, quenched at the same temperature with 250 ml of methanol and allowed to warm to room temperature. The gummy precipitate that formed was filtered through Celite (trademark) and fully washed with stirring with dichloromethane. The solvents were evaporated to dryness to give 70 g of the title compound as an oil. $^1H$ NMR 300 MHz (DMSO-$d_6$): 1.61 (s, 9H); 7.36 (s, 2H); 9.84 (s, 1H); $^{19}F$ NMR 282 MHz (DMSO-$d_6$): −44.10, singlet.

Step D: Preparation of 1-(N-tert-butoxycarbonyl)-3-hydroxyiminoformyl-4-trifluoromethylsulfenyl-5-aminopyrazole The product of Step C (70 g, 225 mmoles) was dissolved in ethanol. 52 g of $NH_2OH \cdot HCl$ and 63 g of sodium hydrogen carbonate were dissolved in water and added at room temperature to the ethanolic solution. The resulting mixture was stirred at room temperature for 2 hours, then concentrated, diluted with ethyl acetate and washed several times with water and brine. The organic layer was dried over $MgSO_4$ and concentrated to dryness to give 66 g of the title compound as a solid (95% yield). $^1H$ NMR 300 MHz (DMSO-$d_6$): 1.58 (s, 9H); 7.19 (s, 2H); 7.94 (s, 1H); 11.80 (s, 1H); $^{19}F$ NMR 282 MHz (DMSO-$d_6$): −44.11, singlet.

Step E: Preparation of 3-cyano-4-trifluoromethylsulfenyl-5-(N-trifluoroacetylamino)pyrazole The product of Step D (66 g, 203 mmoles) was dissolved in methyl tert-butyl ether and 65 ml of pyridine. 95 ml of trifluoroacetic anhydride were added dropwise to the previous solution while keeping the reaction below 20° C. (exothermic). The mixture was stirred at room temperature for 15 hrs, then washed several times with water and extracted 5 times with 200 ml of a 10% aqueous solution of sodium hydroxide. The aqueous layers were combined, brought to pH7 with concentrated aqueous hydrochloric acid and re-extracted with ethyl acetate. The organic layers were combined, dried over $MgSO_4$ and concentrated to dryness to give 55 g of the title compound as an oil. $^{19}F$ NMR 282 MHz ($CD_3CN$): (−42.66, s, $SCF_3$); (−73.54, s, $CF_3CO$).

Step F: Preparation of 3-cyano-4-trifluoromethylsulfenyl-5-aminopyrazole

The product of Step E (55 g, 181 mmoles) was dissolved in methanol. 100 ml of ammonium hydroxide were added, the solution was refluxed for 3 hours and then stirred at room temperature for 15 hours. The methanolic solution was brought to pH7 using concentrated aqueous hydrochloric acid and diluted with ethyl acetate. The organic layer was washed several times with water and brine, dried over $MgSO_4$ and concentrated to dryness to give an oily brown residue which was recrystallized from methyl tert-butyl ether to afford 33 g of the title compound, m.p. around 187° C.

A solution of the product of Step F (1.10 g, 5.28 mmol) in tetrahydrofuran under an inert atmosphere was cooled to 0° C. in an ice bath and treated with 15-crown-5 (0.12 g, 0.54 mmol), followed by sodium hydride (0.5 g, 5.94 mmol). The cooling bath was removed and the mixture was stirred for 45 minutes. A solution of 4-chloro-3,5-dinitrobenzotrifluoride in tetrahydrofuran was added. After 20 min, the mixture was quenched with water, then diluted with ether and washed with water and brine. The combined aqueous washings were extracted with ether, and the combined ethereal solutions were dried over magnesium sulfate, filtered, and evaporated. Purification by column chromatography provided 0.90 g of 5-amino-3-cyano-1-(2,6-dinitro-4-trifluoromethylphenyl)-4-trifluoromethylsulfenylpyrazole m.p. around 214° C.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A process for the preparation of a heterocyclic compound of the formula:

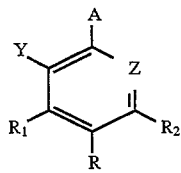

(I)

wherein:

R is haloalkyl, haloalkoxy, haloalkylsulfenyl, haloalkylsulfinyl, haloalkylsulfonyl, F, Cl, Br, I or $SF_5$;

$R_1$ and $R_2$ are each independently hydrogen, F, Cl, Br or I;

Y is F, Cl, Br or I;

Z is N, C—$NO_2$ or C—$R_3$ wherein $R_3$ is H, F, Cl, Br, I, CN, C(O)$NH_2$, C(S)$NH_2$, alkyl or haloalkyl;

and A represents an optionally substituted N-linked nitrogen-containing, five- or six-membered heterocyclic ring;

said process comprising reacting a nitro-containing compound of the formula:

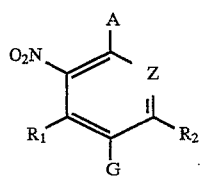

(II)

wherein $R_1$, $R_2$, Z and A are defined as above, and G is haloalkyl, haloalkoxy, haloalkylsulfenyl, haloalkylsulfinyl, haloalkylsulfonyl, F, Cl, Br, I, $SF_5$ or $NO_2$; with a metallic halide of the formula $MX_n$ wherein M is a metal cation, X is a halide anion and n is a positive integer equal to the valence of the metal cation, in the presence of a nitrite ion scavenging agent.

2. A process according to claim 1, wherein the reaction is carried out in the presence of from about 1 to about 3 molar equivalent of nitrite ion scavenging reagent per mole of starting reactant.

3. A process according to claim 1, wherein the nitrite ion scavenging agent is sulfamic acid, urea, aniline, hydroxylamine, hydrazine, hydrazoic acid, ascorbic acid, ammonium sulfamate or ammonia.

4. A process according to claim 3, wherein the nitrite ion scavenging agent is sulfamic acid.

5. A process according to claim 1, wherein the compound of formula (II) has two nitro groups.

6. A process according to claim 5, wherein one nitro group in the compound of formula (II) is replaced by a halogen atom in the course of the reaction.

7. A process according to claim 5, wherein both nitro groups in the compound of formula (II) are replaced by halogen atoms in the course of the reaction.

8. A process according to claim 7, wherein, in a first step, the dinitro compound of formula (II) in which Z is —$NO_2$ reacts with a metal halide salt $MX_n$ to form a monohalo, mononitro compound, and, in a second step, the resultant monohalo, mononitro compound reacts with a metal halide salt $M'X'_n$, wherein the metal cation M' is the same as or different from M and the halide anion X' is the same as or different from X.

9. A process according to claim 1, wherein $MX_n$ is an alkali metal or alkaline-earth metal halide salt.

10. A process according to claim 8, wherein $MX_n$ is an alkali metal or alkaline-earth metal halide salt.

11. A process according to claim 9, wherein $MX_n$ is an alkali metal salt.

12. A process according to claim 10, wherein $MX_n$ is an alkali metal salt.

13. A process according to claim 11, wherein $MX_n$ is LiCl.

14. A process according to claim 12, wherein $MX_n$ is LiCl.

15. A process according to claim 1, wherein the compound of formula (II) is reacted with at least one molar equivalent of $MX_n$.

16. A process according to claim 1, wherein the compound of formula (II) is reacted with from about 1 to about 10 molar equivalents of $MX_n$.

17. A process according to claim 1, wherein the compound of formula (II) is reacted with at least one molar equivalent of $MX_n$.

18. A process according to claim 16, wherein $MX_n$ is LiCl.

19. A process according to claim 17, wherein $MX_n$ is LiCl.

20. A process according to claim 1, wherein the reaction is carried out in the presence of an inert solvent and at a temperature of from about 50° to about 250° C.

21. A process according to claim 1, wherein R is F, Cl, Br, I, $SF_5$ or lower haloalkyl.

22. A process according to claim 21, wherein R is $SF_5$ or $CF_3$.

23. A process according to claim 1, wherein $R_1$ and $R_2$ are both hydrogen.

24. A process according to claim 1, wherein Y is F, Cl or Br.

25. A process according to claim 24, wherein Y is Cl.

26. A process according to claim 1, wherein Z is C—$NO_2$, C—Cl, C—H, C—Br, C—F or C—CN.

27. A process according to claim 1, wherein G is F, Cl, Br, I, $SF_5$ or lower haloalkyl.

28. A process according to claim 27, wherein G is $CF_3$ or $SF_5$.

29. A process according to claim 1, wherein:

R is F, Cl, Br, I, $SF_5$ or lower haloalkyl;

$R_1$ and $R_2$ are both hydrogen;

Y is F, Cl or Br;

Z is C—$NO_2$, C—Cl, C—H, C—Br, C—F or C—CN; and

G is F, Cl, Br, I, $SF_5$ or lower haloalkyl.

30. A process according to claim 29, wherein R is $CF_3$ or $SF_5$, Y is Cl and G is $CF_3$ or $SF_5$.

31. A process according to claim 1, wherein A has the formula:

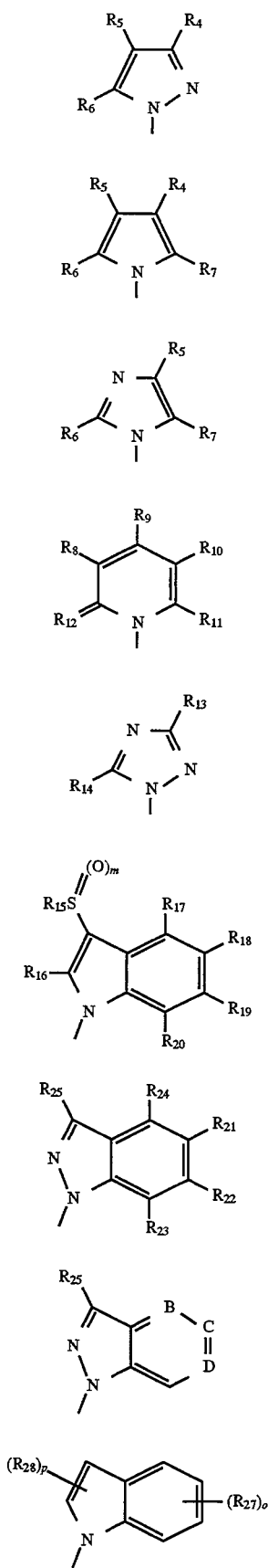

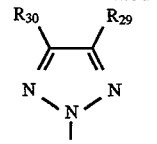(a)

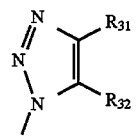(k)

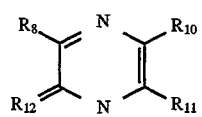(l)

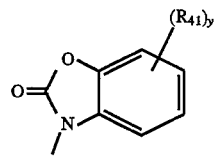(m)

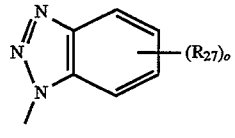(n)

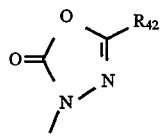(p)

(q)

wherein:

$R_4$ is H, alkyl, haloalkyl, formyl, alkylcarbonyl, halogen, CN, $NO_2$, cycloalkyl, $C(O)NH_2$, alkoxy or $C(S)NH_2$;

$R_5$ is $R_{33}S(O)_q$, CN, SCN, $NO_2$, haloalkyl, haloalkylcarbonyl, haloalkoxy or halogen;

$R_6$ is H, alkyl, haloalkyl, alkylcarbonyl, formyl, haloalkylcarbonyl, halogen, $NR_{34}R_{35}$, alkylsulfenyl, alkylsulfinyl, alkylsulfonyl, alkoxy, haloalkoxy, N=CH—O-alkyl; or N=CH-phenyl optionally substituted with OH, alkoxy, halogen, alkyl, haloalkyl, CN or $NO_2$;

$R_7$ is H, alkyl, haloalkyl, halogen, cyano, alkylsulfenyl, alkylsulfinyl, alkylsulfonyl, haloalkylsulfenyl, haloalkylsulfinyl or haloalkylsulfonyl;

$R_9$ is haloalkyl, CN, $NO_2$, halogen, H, alkylsulfenyl, alkylsulfinyl, alkylsulfonyl, haloalkylsulfenyl, haloalkylsulfinyl, haloalkylsulfonyl or haloalkoxy;

$R_8$, $R_{10}$ and $R_{11}$ are each independently H, alkyl, halo, CN, $NO_2$ or haloalkyl;

$R_{12}$ is O or S;

$R_{13}$ is alkyl, optionally substituted by halogen, alkoxy, alkylthio, alkylsulfonyl, alkoxycarbonyl, carbamoyl, cycloalkyl or alkenyl;

$R_{14}$ is H, halogen, haloalkyl, alkoxyalkyl, alkenyloxyalkyl, methyl, alkylsulfenyl, alkylsulfinyl, alkylsulfonyl or $NR_{34}R_{35}$;

$R_{15}$ is alkyl or haloalkyl;

$R_{16}$, $R_{17}$, $R_{18}$, $R_{19}$ and $R_{20}$ are each independently H, alkyl, alkenyl, alkynyl, halogen, CN, formyl, alkylcarbonyl, alkoxycarbonyl, haloalkoxycarbonyl, haloalkylcarbonyl, $NO_2$, SCN, haloalkyl, alkoxy, haloalkoxy, haloalkenyl, alkylsulfenyl, alkylsulfinyl, alkylsulfonyl, haloalkylsulfenyl, haloalkylsulfinyl or haloalkylsulfonyl;

$R_{21}$, $R_{22}$ and $R_{24}$ are each independently H, halogen, $NO_2$, OH, CN, alkyl, alkoxyiminoalkyl, alkoxyalkyl, haloalkyl or alkoxy;

one of B, C and D is N or N→O and the others of B, C and D are each C—$R_{36}$;

$R_{23}$ is H, halogen, alkyl or $NO_2$;

$R_{25}$ is H or halogen;

$R_{27}$ is H; halogen; $NO_2$; CN; alkyl; alkoxy; alkenyloxy; alkynyloxy; alkoxyalkyl; carbonylalkoxy; alkyloxyalkoxy; cyanoalkoxy; benzyloxy; alkoxycarbonylalkoxy; alkylcarbonylalkoxy; haloalkyl; hydroxyalkyl; formyl; azido; COOH or a salt thereof; COO-alkyl; $NH_2$, which is optionally substituted by alkyl, alkoxy, OH, formyl; alkylcarbonyl optionally substituted by COOH or alkoxycarboxy; alkylsulfonyl, haloalkylsulfonyl, aminocarbonyl, diallcylaminocarbonyl, alkoxycarbonyl, alkoxyalkyl, hydroxycarbonylalkyl, alkoxycarbonylalkyl, amino or dialkylamino; carboxamido, which is optionally substituted by alkyl or haloalkylsulfonyl; sulfonamido in which the N is optionally substituted by alkyl; or $QR_{38}$;

$R_{28}$ is H, alkyl, halogen, CN, haloalkyl or alkoxy, or COOH or a salt or ester thereof;

$R_{29}$ and $R_{30}$ are each independently hydrogen, alkyl, alkenyl, alkynyl wherein alkyl, alkenyl and alkynyl are each optionally substituted with halogen; phenyl, pyridyl, cyano, halogen, nitro, CHO, or $NR_{39}R_{40}$;

$R_{31}$ and $R_{32}$ are each independently H, halogen, CN, $NO_2$, $CONH_2$, alkylsulfinyl, alkylsulfonyl, alkylsulfenyl or $NR_{34}R_{35}$;

$R_{33}$ is $C_1$–$C_6$ alkyl, cycloalkyl, cycloalkylalkyl or haloalkyl;

$R_{34}$ and $R_{35}$ are each independently H, alkyl, alkylcarbonyl, formyl or alkoxycarbonyl, or $R_{34}$ and $R_{35}$ together with the nitrogen atom to which they are attached form a 5-membered pyrrole or pyrazole moiety;

$R_{36}$ is H, halogen, $NO_2$, CN, alkyl, alkoxyalkyl, acetoxymethyl, hydroxymethyl, haloalkyl, formyl, alkylcarbonyl, carboxy or a salt thereof, COO-alkyl, $N_3$; $NH_2$ optionally substituted by alkyl, alkoxy, OH, formyl, alkylcarbonyl, alkoxycarbonylalkyloxy, alkoxycarbonylalkylthio, alkoxycarbonylalkylidenecarbonyl, hydroxycarbonylalkoxy, hydroxycarbonylthio, cyanoalkoxy, hydroxycarbonylalkylidenecarbonyl, alkylsulfonyl, haloalkylsulfonyl, aminocarbonyl, dialkylaminocarbonyl, alkoxycarbonyl, alkoxyalkyl, hydroxycarbonylalkyl, alkoxycarbonylalkyl or amino; carboxyamido optionally substituted by alkyl, alkylsulfonyl or haloalkylsulfonyl; sulfonamido in which the N is optionally substituted by alkyl; or $QR_{37}$;

$R_{37}$ is H, alkyl, haloalkyl, cyanoalkyl, alkoxycarbonylalkyl, hydroxycarbonylalkyl; or aminocarbonylalkyl in which the N is optionally substituted by alkyl;

Q is O or $S(O)_m$;

$R_{38}$ is H, haloalkyl, cyanoalkyl, alkoxycarbonylalkyl, hydroxycarbonylalkyl; or aminocarbonylalkyl in which the N is optionally substituted by alkyl;

$R_{39}$ and $R_{40}$ are independently each hydrogen, optionally substituted alkyl, acyl or aryl, or together with the nitrogen to which they are attached, form a 5- to 7-membered ring which optionally has other hetero ring atoms;

$R_{41}$ is hydrogen, alkyl, alkoxy, alkenyloxy, alkynyloxy, carboxyalkoxy, alkoxycarbonylalkoxy, alkoxyalkoxy, cyanoalkoxy, haloalkylsulfonylamino, alkylsulfonylamino, alkoxycarbonyl, haloalkyl, halogen, nitro, carboxy, carboxyalkyl, hydroxy, benzyloxy or cyano;

$R_{42}$ is $C_7$ bicycloalkyl, methyl- or chloro-substituted $C_3$–$C_6$ cycloalkyl, $C_2$–$C_5$ alkenyl, methyl-substituted $C_6$ cycloalkenyl, 2-methyl-1,3-dithiolan-2-yl or $C_1$–$C_5$ alkyl, wherein alkyl is optionally substituted with halogen, $C_1$–$C_3$ alkoxy, $C_1$–$C_3$ alkylthio, $C_1$–$C_3$ alkylsulfinyl, $C_1$–$C_3$ alkylsulfonyl or $C_1$–$C_3$ alkoxycarbonyl;

m is 0, 1 or 2;

o is 0, 1, 2, 3 or 4;

p is 0, 1 or 2;

q is 0, 1 or 2; and y is 0, 1, 2 or 3.

32. A process according to claim 31, wherein:

R is F, Cl, Br, I, $SF_5$ or lower alkyl;

$R_1$ and $R_2$ are both hydrogen;

Y is F, Cl or Br;

Z is C—$NO_2$, C—Cl, C—H, C—Br, C—F or C—CN; and

G is F, Cl, Br, I, $SF_5$ or lower haloalkyl.

33. A process according to claim 32, wherein R is $CF_3$ or $SF_5$, Y is Cl and G is $CF_3$ or SF5.

34. A process according to claim 31, wherein A has structure (a), (b) or (c).

35. A process according to claim 34, wherein A has structure (a).

* * * * *